(12) United States Patent
Miller et al.

(10) Patent No.: US 7,780,892 B2
(45) Date of Patent: Aug. 24, 2010

(54) TAMPON APPLICATOR WITH IMPROVED FINGERGRIP AND METHOD OF MAKING SAME

(75) Inventors: Michael L. Miller, Dover, DE (US); Wayne David Melvin, Felton, DE (US)

(73) Assignee: Playtex Products, Inc., Westport, CT (US)

( * ) Notice: Subject to any disclaimer, the term of this patent is extended or adjusted under 35 U.S.C. 154(b) by 701 days.

(21) Appl. No.: 11/355,289

(22) Filed: Feb. 15, 2006

(65) Prior Publication Data
US 2006/0135905 A1  Jun. 22, 2006

Related U.S. Application Data

(62) Division of application No. 10/463,202, filed on Jun. 17, 2003.

(60) Provisional application No. 60/390,309, filed on Jun. 21, 2002.

(51) Int. Cl.
*B28B 3/02* (2006.01)

(52) U.S. Cl. .......... 264/293; 264/320; 604/15; 604/16; 604/18; 604/385.17; 604/385.18; 604/904; 138/177

(58) Field of Classification Search .......... 264/293, 264/320; 239/33; 220/705; 604/904, 15, 604/16, 18, 385.17, 385.18; 28/118; D24/141, D24/125; 425/290; 138/177
See application file for complete search history.

(56) References Cited

U.S. PATENT DOCUMENTS

| | | | |
|---|---|---|---|
| 2,489,502 A | 11/1949 | Howard | |
| 3,641,884 A * | 2/1972 | Jivoin | 493/435 |
| 3,696,812 A | 10/1972 | Jaycox | |
| 3,895,634 A * | 7/1975 | Berger et al. | 604/14 |
| 3,899,198 A * | 8/1975 | Maroschak | 285/27 |
| 4,412,833 A | 11/1983 | Wiegner et al. | |
| 4,453,925 A | 6/1984 | Decker | |
| 4,498,899 A | 2/1985 | Gross | |
| 4,508,531 A | 4/1985 | Whitehead | |

(Continued)

FOREIGN PATENT DOCUMENTS

EP  551758  7/1993

(Continued)

OTHER PUBLICATIONS (Translation of) Japanese Office Action dated Apr. 15, 2008 for Japanese Patent Application No. 2004-516297.

(Continued)

*Primary Examiner*—Khanh Nguyen
*Assistant Examiner*—Saeed M Huda
(74) *Attorney, Agent, or Firm*—Ohlandt, Greeley, Ruggiero & Perle, L.L.P.

(57) ABSTRACT

The present invention provides a tampon applicator barrel having a fingergrip with one or more gripping structures that have an acute edge for improved gripping. Preferably, the one or more gripping structures are one or more embossed ring-like structures. The present invention also provides a method for forming the one or more gripping structures on the applicator barrel. The method preferably includes forming at least one embossed ring-like gripping structure on the barrel such that the radial compressive strength of the applicator barrel is not compromised.

13 Claims, 3 Drawing Sheets

U.S. PATENT DOCUMENTS

| | | | |
|---|---|---|---|
| 4,573,963 A | | 3/1986 | Sheldon |
| 4,587,874 A | * | 5/1986 | Lupke et al. ................... 83/340 |
| 4,755,164 A | | 7/1988 | Hinzmann |
| 5,158,535 A | | 10/1992 | Paul et al. |
| 5,279,541 A | | 1/1994 | Frayman et al. |
| 5,290,501 A | | 3/1994 | Klesius |
| 5,330,421 A | | 7/1994 | Tarr et al. |
| 5,346,468 A | | 9/1994 | Campion et al. |
| 5,348,534 A | | 9/1994 | Tomaszewski et al. |
| 5,389,067 A | | 2/1995 | Rejai |
| 5,395,308 A | | 3/1995 | Fox et al. |
| 5,395,309 A | | 3/1995 | Tanaka et al. |
| 5,437,628 A | | 8/1995 | Fox et al. |
| 5,554,108 A | | 9/1996 | Browning et al. |
| 5,558,631 A | | 9/1996 | Campion et al. |
| 5,571,540 A | | 11/1996 | Weyenberg et al. |
| 5,599,293 A | | 2/1997 | Orenga et al. |
| 5,614,230 A | | 3/1997 | Weyenberg et al. ......... 425/393 |
| 5,643,196 A | | 7/1997 | Child et al. |
| 5,683,358 A | | 11/1997 | Nielsen et al. |
| 5,702,553 A | | 12/1997 | Iskra et al. |
| 5,709,652 A | | 1/1998 | Hagerty |
| 5,738,646 A | | 4/1998 | Fox et al. |
| 5,800,377 A | | 9/1998 | Campion et al. |
| 5,823,988 A | | 10/1998 | Orenga et al. |
| 5,891,081 A | * | 4/1999 | McNelis et al. ............... 604/14 |
| 5,931,803 A | * | 8/1999 | Jackson ....................... 604/15 |
| 6,019,743 A | | 2/2000 | Cole et al. |
| 6,024,716 A | | 2/2000 | Rajai |
| 6,045,526 A | | 4/2000 | Jackson |
| 6,095,998 A | | 8/2000 | Osborn, III et al. |
| 6,171,426 B1 | | 1/2001 | Blandhard |
| 6,179,802 B1 | | 1/2001 | Jackson |
| 6,264,626 B1 | | 7/2001 | Linares et al. |
| 6,302,861 B2 | | 10/2001 | Tweddell, III et al. |
| 6,302,862 B1 | | 10/2001 | Osborn, III et al. |
| 6,450,986 B1 | | 9/2002 | Binner et al. ................... 604/15 |
| 6,478,764 B1 | | 11/2002 | Suga |
| 6,511,452 B1 | | 1/2003 | Rejai et al. |
| 6,830,554 B2 | | 12/2004 | Jackson et al. |
| 6,890,324 B1 | | 5/2005 | Jackson et al. |
| 2001/0014784 A1 | | 8/2001 | Tweddell, III et al. |
| 2001/0054820 A1 | * | 12/2001 | Starita ........................ 285/364 |
| 2002/0010413 A1 | * | 1/2002 | Binner et al. ................... 604/15 |
| 2002/0177801 A1 | | 11/2002 | Jackson et al. |
| 2002/0188283 A1 | | 12/2002 | Binner et al. ............... 604/904 |
| 2002/0193726 A1 | | 12/2002 | Cimber ........................ 604/11 |
| 2005/0020964 A1 | | 1/2005 | Melvin et al. |

FOREIGN PATENT DOCUMENTS

| | | |
|---|---|---|
| EP | 605016 | 11/1999 |
| GB | 2166656 A | 5/1986 |
| JP | 1981-102439 | 1/1983 |
| JP | 1994-197927 | 7/1994 |
| JP | 7000451 | 6/1995 |
| JP | 1998-511585 | 11/1998 |
| WO | WO 0197735 A1 | 12/2001 |

OTHER PUBLICATIONS

Office Action from U.S. Appl. No. 10/463,202 dated Oct. 4, 2005.
Office Action from U.S. Appl. No. 10/463,202 dated May 2, 2006.
Office Action from U.S. Appl. No. 10/463,202 dated May 25, 2007.
Office Action from U.S. Appl. No. 10/463,202 dated Nov. 1, 2007.
Office Action from U.S. Appl. No. 10/463,202 dated Apr. 28, 2008.
Office Action from U.S. Appl. No. 10/463,202 dated Nov. 21, 2008.
Office Action from U.S. Appl. No. 10/463,202 dated Jun. 19, 2009.
Definition of "acute", The American Heritage Dictionary (2 pages).
Definition of "acute", Merriam Webster OnLine (1 page).
Definitions of "abut" and "contiguous", Merriam Webster OnLine (4 pages).
Office Action from U.S. Appl. No. 10/463,202 dated Apr. 22, 2010.

* cited by examiner

TAMPON APPLICATOR WITH IMPROVED FINGERGRIP AND METHOD OF MAKING SAME

CROSS-REFERENCE TO RELATED APPLICATIONS

This application is a division of U.S. application Ser. No. 10/463,202, filed Jun. 17, 2003, that claims priority to Provisional Patent Application Ser. No. 60/390,309, filed Jun. 21, 2002, the disclosures of which are incorporated herein by reference.

BACKGROUND OF THE INVENTION

1. Field of the Invention

The present invention relates generally to a catamenial device or applicator with an improved fingergrip. More particularly, the present invention relates to an applicator with an improved embossed fingergrip and a method for making the improved embossed fingergrip.

2. Description of the Prior Art

A catamenial insertion device or applicator normally has two components, namely a barrel and a plunger that is adapted to telescopically slide in the barrel. The material to be expelled, such as an absorbent pledget, is positioned in the barrel of the applicator. The barrel has a first end for ejection of the pledget, and a second end for receipt of the plunger. To use the tampon applicator, the consumer will grasp the barrel near the second end, position the ejection end appropriately, insert the majority of the barrel into the vaginal canal, and move or slide the plunger in the barrel towards the ejection end of the barrel to expel the pledget.

Tampon pledgets, and notably radially expanding pledgets, due to their design, exert a pressure or friction force on the inside wall of the applicator barrel. Thus, expulsion of the pledget from the barrel requires an applicator with a gripping configuration conducive to secure holding by the user with minimal pressure being applied to the barrel. The significance of minimizing pressure on the barrel of the applicator is that deformation of the barrel is reduced. Such barrel deformation causes significant friction amongst the pledget, barrel, and plunger, thereby significantly impeding the expulsion of the pledget from the barrel.

Various configurations for fingergrip areas on the barrel of an applicator have been proposed to facilitate handling and placement of the applicator, and expulsion of the pledget. One approach is a tampon applicator having a fingergrip that is formed by embossing an outside surface of the barrel of the applicator.

Fingergrips on cardboard tampon applicators, when embossed, are generally embossed into the cardboard from the inside so that raised projections are formed on the outside surface. These projections usually have highly curved or highly angled side walls and do not present an acute edge for secure gripping. Alternatively, holes formed either completely or partially through the fingergrip area of the applicator barrel can create an acute edge for gripping. However, this results in substantially weakening the radial compressive strength of the applicator barrel. Therefore, there exists a risk of the user compressing the applicator barrel while holding the barrel, resulting in additional resistance to the pledget during expulsion from the applicator barrel.

U.S. Pat. No. 5,558,631 to Campion et al. discloses a paper laminate applicator with embossed rings. The embossed rings have a radius of curvature less than 0.060 inches. Campion also discloses that attempting such embossed formations in conventional paper applications would tend to rip, shear or otherwise damage the paper.

U.S. Pat. No. 5,709,652 to Hagerty discloses a tampon applicator with apertures provided in the barrel to provide the acute edge for gripping. However, as noted above, this is known to weaken the radial compressive strength of the fingergrip region of the barrel, which could result in making ejection of the pledget more difficult if the user squeezes the grip too hard and it collapses.

Therefore, there is a need in the art for an embossed fingergrip that not only provides an acute edge for improved gripping, but also does not compromise the radial compressive strength of the barrel. The present invention provides at least one embossed gripping structure with at least one acute gripping edge that not only does not compromise the radial compressive strength of the barrel, but may actually increase the radial compressive strength of the barrel. Also, a novel method of forming such an embossed fingergrip structure is disclosed.

SUMMARY OF THE INVENTION

It is an object of the present invention to provide a tampon applicator barrel with an improved fingergrip.

It is another object of the present invention to provide such a tampon applicator barrel with a fingergrip having one or more embossed gripping structures.

It is still another object of the present invention to provide such a fingergrip with one or more embossed gripping structures having at least one acute edge for improved gripping.

It is a further object of the present invention to provide a method for forming a tampon applicator barrel with a fingergrip having one or more embossed gripping structures with acute edges for gripping.

It is still a further object of the present invention to provide such a method for forming both the one or more embossed gripping structures and a substantially closed petal tip applicator barrel substantially simultaneously.

It is yet a further object of the present invention to provide such a method that maintains and/or improves the radial compressive strength of the tampon applicator barrel.

The above and other objects and advantages of the present invention are provided by a tampon applicator barrel having a fingergrip with one or more gripping structures that have at least one acute edge for improved gripping. Preferably, the one or more gripping structures are one or more embossed, raised, ring-like structures. The present invention also provides a method for forming the one or more gripping structures on the applicator barrel. The method preferably includes forming at least one embossed ring-like structure on the barrel such that the radial compressive strength of the applicator barrel is not compromised.

DETAILED DESCRIPTION OF THE INVENTION

Figure 1:
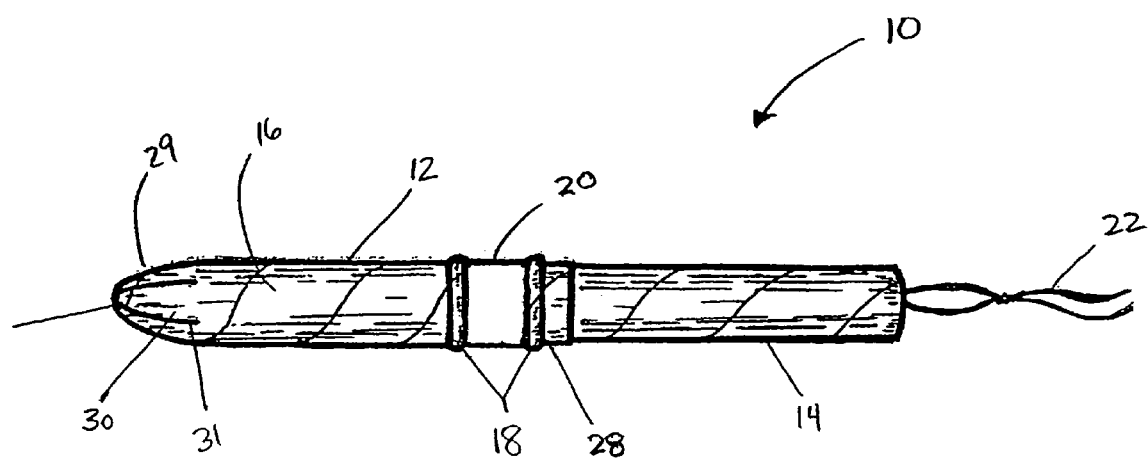
FIG. 1 is a plane view of one embodiment of a tampon applicator according to the present invention.

Referring to the drawings and, in particular, FIG. 1, there is shown a tampon applicator or inserter generally represented by reference numeral 10. Tampon applicator 10 houses and carries a tampon pledget (not shown) having a removal string 22. Tampon applicator 10 has a barrel 12 and a plunger 14 telescopically engageable with the barrel.

Barrel 12 has a central body 16 that is preferably tubular and can house and carry the pledget therein, a forward or ejection end 26, and an opposite, rear or plunger-receiving end 28. The plunger 14 can eject the pledget from barrel 12 out of ejection end 26 of the barrel into the vagina of a user.

Ejection end 26 of barrel 12 can be open or can have a substantially closed tip. The ejection end 26 preferably has a hemispherical, dome-shaped tip 29. The tip 29 may have a number of petals 30, which are preferably formed by a number of slits 31. The petals 30 are flexible, enabling the pledget to be ejected therethrough when plunger 14 is pressed against an end of the pledget within barrel 12.

Figure 2:
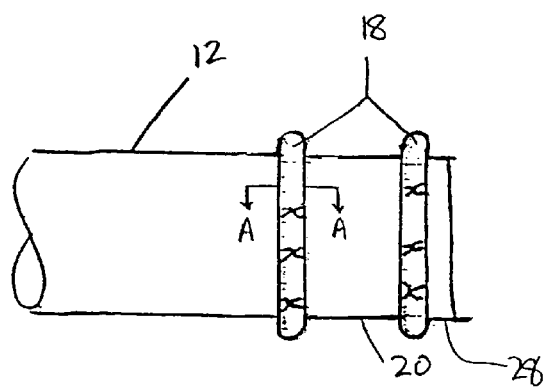
FIG. 2 is an enlarged view of the applicator barrel and gripping structures of the present invention.
Figure 3:
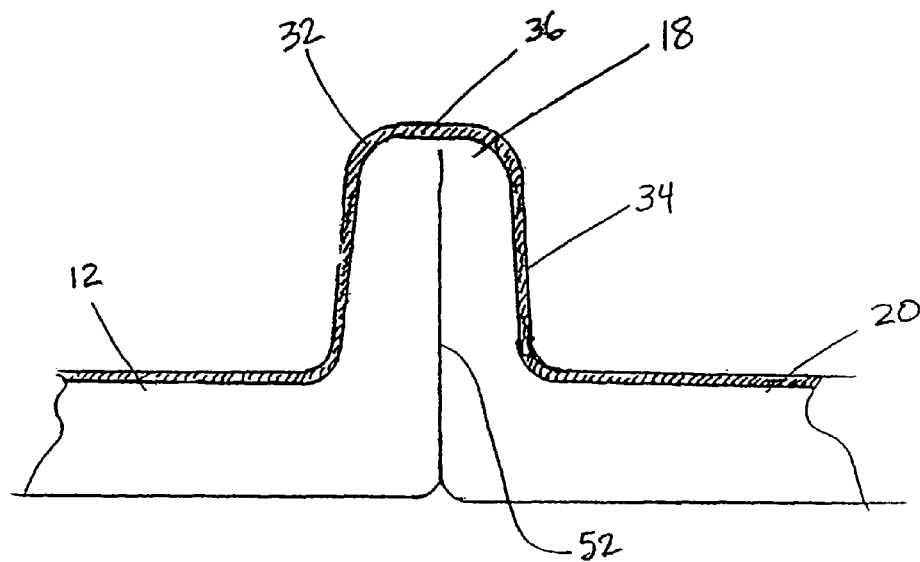
FIG. 3 is a cross-sectional view of the gripping structure taken along line A-A in FIG. 2.

Referring to FIGS. 1 through 3, to improve grippability, barrel 12 preferably has one or more gripping structures 18. Preferably, the one or more gripping structures 18 are disposed on barrel 12 near plunger-receiving end 28. The one or more gripping structures 18 are preferably one or more embossments. The one or more embossments may be formed in any shape suitable for forming one or more gripping structures 18 on barrel 12. Preferably, the one or more gripping structures of the present invention are one or more embossed, ring-like structures.

Referring to FIG. 3, the one or more embossed, ring-like structures have at least one acute edge 32 that improves grippability, thereby making for a more secure grip. The at least one acute edge 32 is formed by a substantially vertical sidewall 34 and a substantially planar top portion 36. It is this substantially vertical sidewall 34 that provides a user with an enhanced or superior grip on barrel 12 during use of applicator 10.

To provide the enhanced grippability, it has been found that the substantially vertical sidewall 34 is tapered, with respect to a perpendicular plane from the base of the sidewall, towards the substantially planar top portion about 0° to at most about 20°.

To further provide enhanced grippability of barrel 12, it has been found that the height of the one or more embossed ring-like structures is about 0.01 inches to about 0.1 inches, and preferably about 0.015 inches to about 0.06 inches. The width of the one or more embossed ring-like structures 18 is about 0.03 inches to about 0.1 inches, and preferably about 0.04 inches to about 0.05 inches.

Barrel 12 and/or plunger 14 of the present invention may be formed from any suitable material known in the art. Suitable materials include, but are not limited to, one or more biopolymers including polysaccharides and proteins, cardboard, heat shrink, paper, paper laminates, cardboard laminates, paper slurry, plastic, plastic tubing, pulp-molded paper, or any combinations thereof.

Additionally, barrel 12 and/or plunger 14 may be coated on the inside and/or the outside surface. The coating may be any suitable material to enhance strength, reduce surface friction, enhance aesthetics, or any combination thereof. Suitable coatings include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

Figure 4:
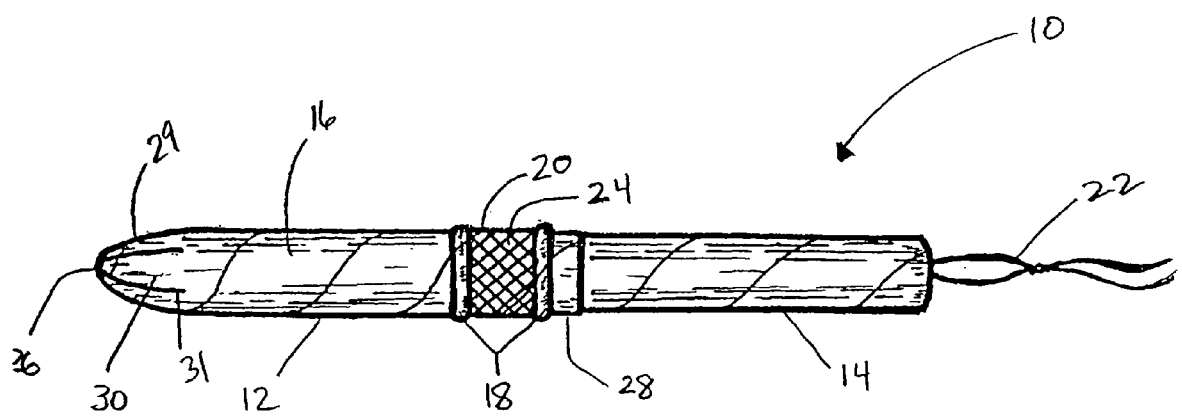
FIG. 4 is a plan view of another embodiment of a tampon applicator of the present invention.

In another embodiment of the present invention, as depicted in FIG. 4, barrel 12 may also have one or more additional gripping structures 24 disposed in a finger-accepting gripping region 20 formed on barrel 12. Preferably, finger-accepting gripping region 20 is formed between two or more gripping structures 18. The one or more additional gripping structures 24 may be any structure suitable for increasing the grippability of barrel 12. The one or more additional gripping structures 24 may be smooth or, more preferably, may include one or more patterned or textured structures. The one or more additional gripping structures 24 may have an apex of the one or more gripping structures extend above and/or below the surface of barrel 12, or may be substantially aligned with the outer surface of barrel 12.

Suitable additional gripping structures 24 may include, but are not limited to, one or more abrasive materials, embossments, grooves, high wet coefficient of friction materials, lances, pressure sensitive adhesives, protuberances, slits, treads, or any combinations thereof. In addition, the one or more additional gripping structures 24 may be formed in any shape, including, but not limited to, arc, circle, concave, cone, convex, diamond, line, oval, polygon, rectangle, rib, square, triangle, or any combinations thereof.

Figure 5:
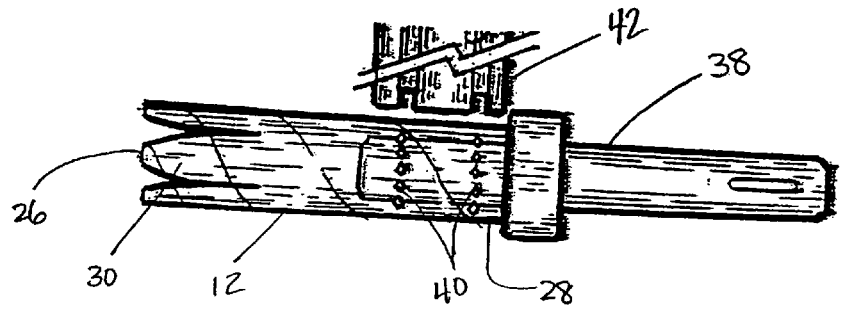
FIG. 5 is a plan view of a tampon applicator barrel of the present invention positioned on a mandrel for embossing.
Figure 6:
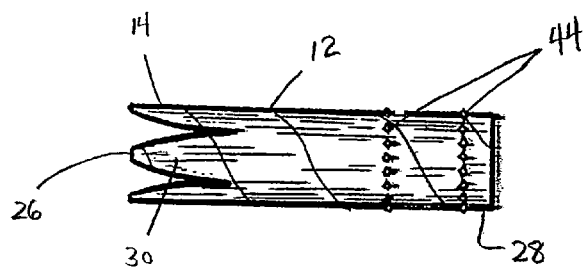
FIG. 6 is a plan view of a tampon applicator barrel with individual embossments formed according to one aspect of the present invention.
Figure 7:
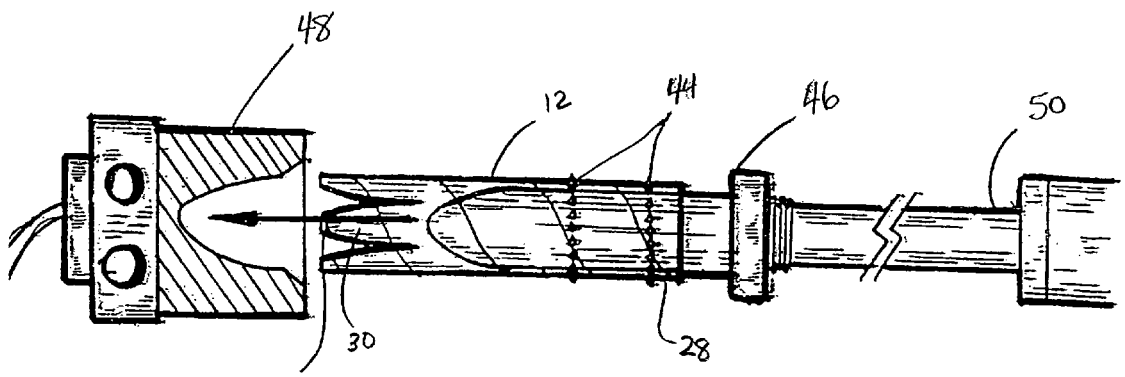
FIG. 7 is a plan view of a tampon applicator barrel prior to forming a petal-tip and embossed ring-like structures according to the present invention.

In another embodiment of the present invention, a novel method for forming the one or more embossed gripping structures is provided. Referring to FIGS. 5 through 7, the method includes embossing barrel 12 such that a pattern of embossments is formed above the surface of the barrel to cause an axially weakened region. Preferably, at least one ring-like pattern is formed circumferentially around barrel 12. The embossing may be accomplished by any embossing process known to those skilled in the art.

In a preferred embodiment of the present invention, as depicted in FIG. 5, mandrel 38, having a punch-through crease pattern 40, is positioned in barrel 12, preferably from plunger-receiving end 28. With mandrel 38 and barrel 12 rotating, downward pressure is applied to the barrel by an upper wheel 42. As a result, a ring-like pattern of embossments 44 is formed on barrel 12, as depicted in FIG. 6.

Preferably, in one embodiment of the present invention, the ring-like pattern of embossments does not form a continuous band, but forms a series of individual embossments 44 aligned substantially in a circumferential row. In another preferred embodiment of the present invention, a petal tip, preferably a substantially closed petal tip, is formed on barrel 12 while forming the one or more embossed fingergrip structures.

Referring to FIG. 7, after the embossing, barrel 12 is placed over a petal-forming mandrel 46. Insertion end 26 of barrel 12 is then positioned in a petal former 48, to form petals 30 on barrel 12. At the same time that the petals 30 are formed, an axial force of sufficient magnitude is applied to barrel 12 at plunger-receiving end 28 to force some of the length of the barrel at the axially weakened region formed by the series of individual embossments to fold back upon themselves, like an accordion. This causes the formation of an outward protuberance, such as, for example, a ridge having at least one acute edge for gripping. It has been found that this invention not only provides one or more embossed gripping structures 18 having at least one acute edge for gripping, it also does not radially weaken barrel 12 at the one or more embossed gripping structures. Accordingly, the radial compressive strength of barrel 12 is not compromised. To the contrary, the radial compressive strength of barrel 12 may be increased since the one or more embossed gripping structures 18 act as stiffening structures.

Grippability can be further increased, if the individual embossments 44 are spaced apart at approximately 2 millimeters (mm) to about 20 mm, and preferably about 3 mm to about 6 mm. Wherever there is an individual embossment, applicator barrel 12 can be made to rupture during axial compression resulting in an acute point. The accordion-like fold between two adjacent embossments tends to be straight and does not exactly follow the radial curvature, if any, of barrel 12.

It should be understood that the fingergrip of the present invention could also be formed on an applicator barrel that has a non-circular cross-sectional fingergrip region, such as, for example, polygonal, flat, or oval cross sections.

If the embossed dots are placed closer together, the rupturing at the dots is less severe. Also, the one or more embossed ring-like gripping structures 18 appear less polygonal when viewed from the end. If the embossed dots are spaced further apart, the amount of rupturing does not significantly increase but the appearance tends to be less aesthetic since the one or more embossed ring-like gripping structures take on a distinct polygonal shape when viewed from the end.

The present invention has been described with particular reference to the preferred forms thereof. It will be obvious to one of ordinary skill in the art that changes and modifications may be made therein without departing from the spirit and scope of the present invention as defined by the following claims.

What is claimed is:

1. A process for forming at least one embossed gripping structure on a tampon applicator barrel, the tampon applicator barrel having an external barrel surface and a finger grip surface adjacent the external barrel surface, the tampon applicator barrel having a tubular wall surrounding an inner volume, the process comprising the steps of:
   positioning a mandrel in the tampon applicator barrel, the mandrel having an outer surface sized to be positioned in the inner volume and having a plurality of individual protrusions aligned circumferentially in a row about the outer surface of the mandrel;
   forming a plurality of individual embossments on the finger grip surface, the plurality of individual embossments each being a protrusion entirely above the external barrel surface of the tampon applicator barrel, the plurality of individual embossments being formed by the plurality of individual protrusions of the mandrel, wherein the plurality of individual embossments results in an axially weakened region in the tampon applicator barrel at the plurality of individual embossments; and
   applying an axial force to a plunger-receiving end of the tampon applicator barrel to fold the plurality of individual embossments back upon themselves at the weakened region thereby forming at least one raised gripping structure that has a first sidewall, a second sidewall and a substantially planar top portion between the first sidewall and the second sidewall formed by the tubular wall.

2. The process of claim 1, wherein the plurality of individual embossments are aligned circumferentially in substantially a row.

3. The process of claim 1, wherein the tubular wall has an inner surface opposite the finger grip surface and the external barrel surface, wherein the forming the plurality of individual embossments further comprises contacting a portion of the finger grip surface with a pressure wheel, wherein the pressure wheel contacts the portion of the outer finger grip surface that is opposite a portion of the inner surface that contacts the plurality of individual protrusions, and wherein the pressure wheel applies a downward force on the portion of the finger grip surface.

4. The process of claim 1, wherein the at least one embossed gripping structure is at least one ring-like gripping structure.

5. The process of claim 1, wherein the barrel has an increased radial compressive strength at the one or more embossed raised gripping structures.

6. A process for forming at least one embossed gripping structure and a tapered petal tip on a tampon applicator barrel, the tampon applicator barrel having an external barrel surface and a finger grip surface adjacent the external barrel surface and being sized to have a tampon pledget therein, the process comprising the steps of:
   (a) forming at least one embossment on the finger grip surface above the external barrel surface of the barrel, wherein the at least one embossment also results in an axially weakened region formed in the barrel at the at least one embossment;
   (b) loading the embossed barrel at a plunger-receiving end of the barrel with a mandrel;
   (c) loading a petal tip of the embossed barrel into a petal former; and
   (d) applying an axial pressure to the plunger-receiving end of the barrel,
   wherein the axial pressure results in a substantially closed petal tip to cover the tampon pledget and the at least one embossed gripping structure formed on the barrel.

7. The process of claim 6, wherein the at least one embossed gripping structure is at least one embossed ring-like gripping structure.

8. The process of claim 6, wherein the substantially closed petal tip and the at least one embossed gripping structure are formed substantially simultaneously.

9. The process of claim 1, wherein the first sidewall is a substantially vertical sidewall that is tapered with respect to a perpendicular plane from a base of the first sidewall towards the substantially planar top portion about 0 degrees to at most about 20 degrees.

10. The process of claim 6, wherein the mandrel has a punch-through crease pattern.

11. The process of claim 6, wherein the at least one embossment is a ring-like pattern of embossments that forms a series of individual embossments aligned substantially in a circumferential row.

12. The process of claim 11, wherein one of the series of individual embossments ruptures during the applying an axial pressure resulting in an acute point.

13. The process of claim 12, wherein the applying an axial pressure forms an accordion-like fold between two adjacent embossments of the series of individual embossments that are straight and do not exactly follow a radial curvature of the barrel.

* * * * *